US00RE39104E

(19) United States
(12) Reissued Patent
Duclos et al.

(10) Patent Number: US RE39,104 E
(45) Date of Reissued Patent: May 23, 2006

(54) PROCESS FOR THE PRODUCTION OF DRY PHARMACEUTICAL FORMS AND THE THUS OBTAINED PHARMACEUTICAL COMPOSITIONS

(75) Inventors: Roselyne Duclos, Bonsecours (FR); Didier Terracol, Verrieres le Buisson (FR)

(73) Assignee: Laboratoires Effik (FR)

(21) Appl. No.: 10/190,499

(22) Filed: Jul. 8, 2002

Related U.S. Patent Documents

Reissue of:
(64) Patent No.: 5,776,495
Issued: Jul. 7, 1998
Appl. No.: 08/670,497
Filed: Jun. 27, 1996

(30) Foreign Application Priority Data

Jul. 26, 1994 (FR) ..... 94-09227
Jul. 27, 1995 (FR) ..... PCT/FR95/01009

(51) Int. Cl.
*A61K 9/66* (2006.01)
*A61K 31/57* (2006.01)

(52) U.S. Cl. ..... 424/455; 514/169; 514/963
(58) Field of Classification Search ..... 424/455, 424/460, 461; 514/169, 963
See application file for complete search history.

(56) References Cited

FOREIGN PATENT DOCUMENTS

| | | |
|---|---|---|
| DE | 1053736 | 3/1959 |
| DE | 2822882 | 12/1978 |
| EP | 0012523 | 6/1980 |
| EP | 0371471 | 6/1990 |
| FR | 385316 | 1/1932 |
| FR | 84468 | 11/1982 |

OTHER PUBLICATIONS

Chiou, W.I. and Riegelman, S. : Pharmaceutical applications of solid dispersion systems. J. Pharmaceutical sciences. vol. 60, pp. 1281–1302, 1971.*
Kassem, M.A.A. et al. : High energy states of Tolnaftate. Egypt. J. Pharm. Sci. vol. 33, pp. 267–281, 1992.*
Pharmaceuticals Article. vol. 116, 1992 p. 449 Derwent 89–088668 (1 page).

* cited by examiner

*Primary Examiner*—Charanjit S. Aulakh
(74) *Attorney, Agent, or Firm*—Muserlian, Lucas and Mercanti

(57) ABSTRACT

A process for the production of a solid dispersion of at least one therapeutic agent in a hydrophilic carrier having enhanced solubility in an aqueous media comprising dissolving at least one therapeutic agent in a volatile organic solvent containing a very hydrophilic polymer and evaporating the solvent to dryness to form a co-precipitate of therapeutic agent and hydrophilic polymer and the resulting products and their therapeutic method of use.

20 Claims, 2 Drawing Sheets

PROCESS FOR THE PRODUCTION OF DRY PHARMACEUTICAL FORMS AND THE THUS OBTAINED PHARMACEUTICAL COMPOSITIONS

Matter enclosed in heavy brackets [ ] appears in the original patent but forms no part of this reissue specification; matter printed in italics indicates the additions made by reissue.

It has been known for several years that by the side of classic exploration of the pharmacological and toxicological properties of the drugs, one takes care more and more on the quantitative aspect of the resorption of the active component. The kinetics become more and more the object of systematic studies because the intensity of the response and sometimes the nature thereof, are a function of the concentration obtained at the level of the site of action. The significance of these studies on pharmacokinetics and bioavailability have shown the interest of the modifications brought during the preparation of the galenic forms, mainly for the ones adapted for administration by the digestive tract.

Drugs with poor solubility in water or hardly salifiable during the passage in the stomach are only partially resorbed. The prior literature has shown that the digestive resorption might be modified in a favorable way by the study of the particle size, by the adjunction of non-ionic surfactants as well as by the adjunction of a solubilizing agent.

The micronization which suitably increases the external specific surface of a powdery product yet constitutes an approach to the problem, is only convenient for some pharmaceutical forms, such as suspensions or soft gelatin capsules. It cannot be a general solution to this problem. The adjunction of surfactants can increase the solubility of active components and thereby, improve the kinetics of resorption, but cannot necessarily allow obtaining higher blood levels. Moreover, it is often necessary to add very important amounts (25 to 50%) of a surfactant to obtain a defined result. This improvement in the passage by the digestive tract seems to result from a decrease in the superficial tension involving an increase of the digestive mucous permeability.

The beneficial effect obtained by adding an emulsifying agent and especially a fatty acid ester of a glucid proceeds from a different principle. This ester increases the molecule lipophily and makes passage through the intestinal barrier more easy to clear. Nevertheless, this type of process gives some result only with very lipophilic molecules and requires high concentrations of such fatty acid esters of glucid.

It is also known that, for active substance absorption, the gastro-intestinal tract level of which is limited due to their low solubility in biological liquids, one of the possibilities offered to the galenist for the improvement of kinetics of dissolution is the production of solid dispersions. These solid dispersions (defined by Chiou et al in J. Pharm. Sci., Vol. 60, pp. 1281–1302, 1971) constitute systems which, depending on the process used for their production, may present different structures (see Ford, Pharm. Acta. Helv., Vol. 61,3, pp. 69–88, (1986) Bloch et al, Pharm. Acta. Helv., Vol. 62, pp. 23–27, (-1987)), corresponding to different crystallographic states. The vitreous state, though it is a solid state, draws near to a liquid state for its structural disorder. It is a little orderly state, easy to break and which improves substantially the rate of dissolution for less soluble components. Nevertheless, despite the great number of publications relating to the production of solid dispersions, especially for Macrogols or Poloxamers, this technique has not known any important development because of its lack of generality. In some cases, the rate of dissolution is great. In other cases, the rate of dissolution is weaker and makes one's way toward an asymptotic value. For the same drug and for the same concentration, it has been established very significant variations in rates of solubility in terms of the nature of co-fusing agent and even in certain cases, the impossibility to obtain a complete solubilization of the active component, even after a protracted time of contact.

OBJECTS OF THE INVENTION

It is an object of the invention to provide a novel process for dry pharmaceutical products and the co-precipitate formed thereby which, when administered orally has a faster and greater resorption.

It is another object of the invention to provide improved pharmaceutical compositions and method of use.

These and other objects and advantages of the invention will become obvious from the following detailed description.

THE INVENTION

The novel process of the invention for the production of a solid dispersion of at least one therapeutic agent in a hydrophilic carrier having enhanced solubility in an aqueous media comprises dissolving at least one therapeutic agent in a volatile organic solvent containing a very hydrophilic polymer and evaporating the solvent to dryness to form a co-precipitate of therapeutic agent and hydrophilic polymer.

The fact is that the resorption in the digestive tract takes place over a short time and in a reduced space. It is therefore of importance that, in the formulation of the invention, the active component will be conveyed quickly and completely in a solubilized form as the absorption rate will be dependent therefrom. It appeared that the best absorption kinetics were obtained with dispersions in very hydrophilic polymers and especially in polyvinylpyrrolidone in a co-precipitated form. A dissolution rate of 80% within 10 minutes at least has been obtained. Applicants' studies have shown that the dissolution rate will be increased still more when the organic solvent also contained a surface-active agent which further improves the wetability of the active ingredient and optionally limits the phenomenon of growth of crystals which operates during the conservation of solid dispersions and leads to a decrease of the kinetics of dissolution as a function of time.

Since 1961, date when Sekiguchi et al. Chem. Pharm. Bull., Vol. 9 (1961), pp. 866–872, have proposed for the first time the use of solid dispersion, about 300 publications describing the mode of production of these systems as well as their physico-chemical, galenical, and pharmaceutical properties have issued in the literature. This pharmaceutical technique widely described in the literature, concern more than a hundred of active ingredients dispersed in at least thirty or more various hydrophilic carriers and has been made the subject of many synthetic reviews Bloch et al/Chiou et al/Duchene Pharma., Vol. 1, (11), pp. 1064–1073 (1985)/Ford/Puisieux et al Pharma, Prob. et Tech., Vol. 305, pp. 11–20 (1981).

The solid dispersions are systems in which one or several active ingredients are dispersed in the solid state (microparticular, even molecular) in an inert solid vehicle (Chiou et al). These solid dispersions have to be made distinct from mere mixture of powders designated under the name of physical mixture. Two methods are currently used for the preparation of solid dispersions: the method of melting/solidification which leads to the formation of co-melted—and the method of dissolution/evaporation which leads to the formation of co-precipitates. A mixed method resulting from the combination of both preceding methods, is sometimes cited but appears to be seldom utilized.

The process of the invention utilizes the formation of co-precipitates by means of dissolution—evaporation. The very hydrophilic polymer dissolved in the organic solvent preferably is a polyvinylpyrrolidone having a molecular weight ranging from 10,000 to 5,000, a (N-methylpyrrolidone) or a N-methylpiperidone-2). These selected cyclic lactams are very soluble in water and produce co-precipitates which are easily and wholly soluble in water.

The organic solvent usually is a solvent which both dissolves the very hydrophilic polymer and the active ingredient while having a sufficiently high degree of volatility to be in a position to be after dissolution of the mixture, evaporated off without having recourse to—very strong, physical means—such as heat or vacuum. Such solvents are for example oxygenated solvents such as ethanol, isopropanol, tetrahydrofuran, isopropyl ether, acetone, methy ethyl ketone, tetrahydropyran, or chlorinated solvents such as methylene chloride or even mixtures in various proportions of these same solvents.

The optionally added surface-active agent preferably is a non-ionic surface active agent selected from the polyoxyethylenic esters of sorbitan and saturated or unsaturated fatty acids having at least 8 carbon atoms; polyoxyethylenic ethers of fatty alcohols of at least 8 carbon atoms and the polyoxyethylenic esters of stearic acid.

The non-ionic tensio-active agent is selected from among those having an amphiphilic character but with a hydrophilic predominancy, having a HLB>12, such as the polyoxyethylenic esters of sorbitan and fatty acids such as Tweens 20 to 80, the polyoxyethylenic ethers of fatty alcohols such as the Brijs 56, 58, 78, 96, 97, 98, 99; G 3816 and 3820, G 3910 and 3920 or Ethylan D254 to 257 or Renex or Cremophor as well as those of Pluronic type (block-Copolymers of ethylene oxide and propylene oxide such as Pluronics F 68 and F 87 or Poloxamer 188).

Among the hardly water soluble active ingredients, the incorporation of which in the pharmaceutical compositions of this invention may be retained, these may be cited more particularly.

anti-inflammatories and analgetics
- salsalate
- benorylate
- oxametacine
- piroxicam
- nimesulide
- floctafenine
- ethenzamide immunosuppressants
- cyclosporine anti-histaminics
- terfenadine
- brompheniramine
- chlorpheniramine antifungals and anti-trichomonas
- metronidazole
- ornidazole
- dapsone
- itraconazole antivirals
- cytarabin antipsychotics
- sulpiride
- sultopride hormones
- estradiol and its esters
- estrone
- estriol
- progesterone and its derivatives cardio-vascular agents
- dobutamine
- diltriazem
- nifedipine and analogs anti-ulcerous agents
- pirenzepine anti-bacterial agents
- erythromycin
- flumequine
- oxytetracycline
- piperacillin
- cefuroxime anti-arrhythmic agents
- propafenone
- amiodarone
- cordarone
- flecainide
- gallopamil
- verapamil
- dipyridamole
- diisopyramide anti-migrainous agents
- flunarizine
- derivatives of ergot anti-depressants
- fluvoxamine
- fluanisone anti-hormones
- flutamide broncho-dilators
- tulobuterol
- talinolol
- prenalterol anxiolytics
- thiothixene
- trazodone
- doxepine vaso-dilators
- ethaverine
- pentoxyphylline
- eburnamonine diuretics
- furosenide
- triamterene
- torasemide anti-spasmodics
- flavoxate
- trimebutine agents inhibiting the excretion of calcium
- clodronate
- pamidronate anti-coagulating agents
- pindione
- tromexan and/or hypocholesterolemiants, and more precisely the derivatives of clofibric acid such as for example clofibrate clofibride fenofibrate gemfibrozil benzafibrate and finally mainly metronidazole, itraconazole, cyclosporine, piperacilline and cefuroxime.

Principally, the content of active ingredients in the pharmaceutical composition of this invention is of the same order of magnitude as with the usual pharmaceutical composition.

A more significant attention has to be paid to the compounds which are little or not resorbed in the intestines such as progesterone and its derivatives. It is preferred that the substitution in 17 α is needed in order that the progesteronic agents are active orally (cyproterone acetate, demegestone, promegestone, norethynodiol diacetate, medroxyprogesterone acetate . . . ) but this substitution has an effect to induce at the same time, noxious side-effects (androgenic or anti-androgenic action, estrogenic action . . . ) which are not at all desired. It appears highly desirable to use native progesterone or a derivative of progesterone such as dihydroesterone, 17α-hydroxyprogesterone for example, which does not bear any supplemental substituent in position 17α.

The resorption of such molecules is made easier by incorporating them in the form of a solid dispersion of the invention in an outer shell in the presence or absence of surface-active agents. In such a medium, the progesteronic derivative easily and quickly dissolves in the presence of water.

In the case of progesteronic derivatives, one may realize co-precipitates containing from 10 to 60% by weight of active ingredient. The amount of surface active agent ranges from 0.5 to 20% related to the whole mass. The preferred content ranges from 15 to 35% for the progesteronic derivative and from 1 to 10% of surface-active related to the whole mass. Co-precipitates of progesteronic derivatives are obtained which dissolve practically in an integral manner in water or in an aqueous medium in 10 to 20 minutes under stirring, depending on the content of progesteronic derivative.

Studies performed by the applicants have shown that: A) The presence of surface active agents such as polysorbate 80, improves the rate of release of the progesteronic derivative whatever is the co-precipitate. This improvement is all the more significant because the content of active ingredient increases in the sample. It is then for example that the average levels of dissolution of the progesteronic derivative in the co-precipitates having 30 and 50% w/w active ingredient with polysorbate, respectively are 95 and 60% in 10 minutes as compared with 55 and 18% for the same samples prepared without polysorbate. B) The rate of dissolution of the progesteronic derivative is independent of the content of polysorbate 80 in the co-precipitates with 20 and 30% w/w of active ingredient because the kinetics are practically superimposable. On the other hand, this rate of dissolution depends on the percentage in weight of polysorbate 80 for the co-precipitates at 50% w/w.

The best kinetics are obtained with the sample containing 10% w/w of polysorbate 80. This result shows that a more significant amount of surface active agent is required to facilitate the wetting and the dissolution of a progesteronic derivative when its content is high in the co-precipitate.

However, it has been determined that during their storage, the solid dispersions are susceptible to evolve to more thermodynamically stable states by recrystallization or growth of dispersed particles, knowing that time and temperature factors have a significant effect on this transformation, and it appears necessary to study the future of the co-precipitates of progesterone/PVP and progesterone/PVP/polysorbate 80 after 6 months of storage at different temperatures. The results of the studies have shown that the kinetics of dissolution of the progesteronic derivative obtained from co-precipitates stored 6 months at 4° C., 20° C., and 37° C. do not present significative differences with freshly prepared products whatever the temperature of preservation is and whatever the concentration of active ingredients of the kinetics of dissolution in the case of progesterone is.

When the organic solution brought to dryness is ground, the resulting pulverulent product can be diluted with carriers or pharmaceutical vehicles or be subjected to a coating by fluidized bed. The achieved pharmaceutical forms can be packed in the form of tablets, sugar-coated pills, pills, soft gelatin capsules or sachets according to the usual technics of the industrial galenics. It is also possible to form by coating in a fluidized bed a granule which can be broken, screened and compressed or kept intact, and which can be divided in tight sachets ready for administration.

Figure 1:
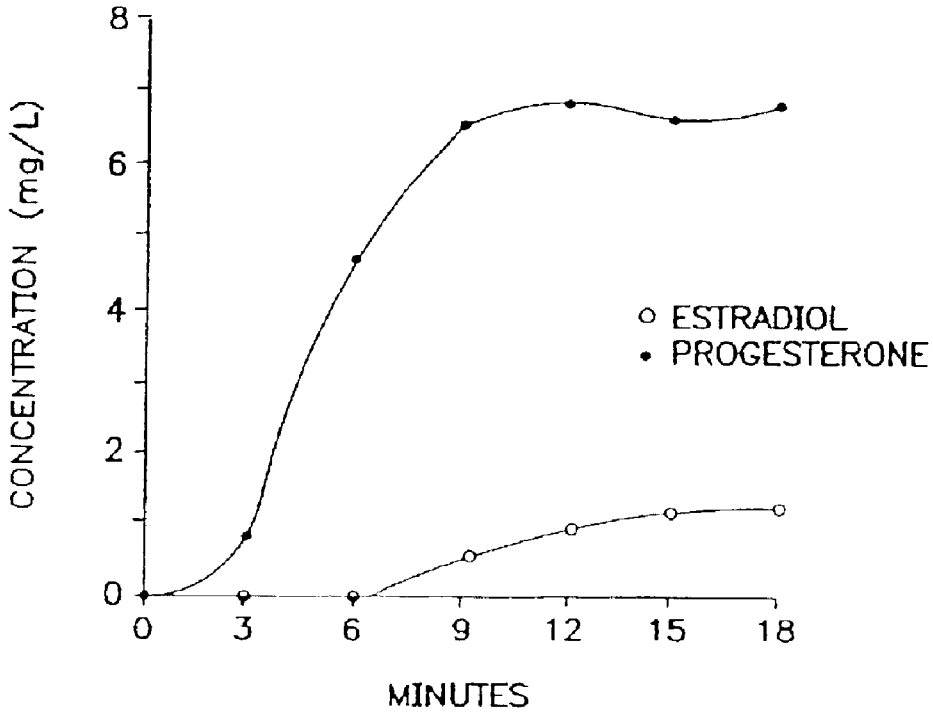
FIGS. 1 and 2 are graphs showing the dissolution in water of 200 grams of powder per liter.

In the following examples, there are described several preferred embodiments to illustrate the invention. However, it should be understood that the invention is not intended to be limited to the specific embodiments.

The performed tests have thus had as an aim to improve the kinetics of dissolution of an active ingredient such as progesterone to improve the bioavailability of this hormone after oral administration. In a first part, a number of solid dispersions have been prepared by the method of melting/solidification and or by the method of dissolution/evaporation using five hydrophilic excipients: saccharose distearate, polyoxyethyleneglycol 4000, polyvinyl pyrrolidone, citric acid, and phospholipids. The thus-finalized techniques have allowed to obtain, in a reproducible manner, products showing a clear improvement in the dissolution of progesterone.

Physical mixtures containing 20, 30 and 50% w/w of progesterone have been prepared with polyvinyl pyrrolidone (Kollidon 30 BASF) while replacing respectively 1, 5 or 10% w/w of PVP with the corresponding amount of polysorbate 80. The process of manufacture of these samples without a tensio-active agent but the physical mixture is dissolved in a sufficient amount of absolute ethanol contained in the solution, polysorbate 80. The conditions for evaporating the solvent are those previously listed and the co-precipitates also show the appearance of a white, crumbly and easily recoverable foam. The optimal diluent for the forthcoming of this study has been polyvinylpyrrolidones with which a co-precipitate containing 20% w/w of progesterone, shows a rate of dissolution of 80% in 10 minutes.

In a second part, it has been tried to further optimize the formulation of the co-precipitates of progesterone/PVP by modifying, on one side, the concentration of the active ingredient in the samples, and/or the conditions of evaporation of the solvent, and studying on the other side, the influence of the surface-active agent incorporated in the formulation at various concentrations. It has been stated that polysorbate 80 or Cremophor EL very significatively improved the rate of dissolution of progesterone. The best results have been obtained with the more concentrated co-precipitates.

In a third part, it has been evidenced that the kinetics of dissolution of progesterone after 6 months storage at 4° C., 20° C. and 37° C., do not significantly change in comparison with those recorded with the freshly prepared products when the samples contained polysorbate 80. However, as regard to the samples prepared without polysorbate 80, the increase of the temperature may be a factor unfavorable for the good conservation of the samples, even when the observed change results in the improvement of the kinetics of dissolution of progesterone. It may then be assumed that for temperatures near 37° C., some changes in the physical properties of the co-precipitates appear, as for example, a vitreous transition which thus promotes the release of the active ingredient.

From the entire results, it appears that the co-precipitates with 30 to 50% w/w of polysorbate 80 in PVP show good galenical characteristics. In fact, the rates of dissolution of the hormone after storage are superposable to those obtained with a freshly prepared product on one side, and provide, on the other side, a rate of dissolution higher than 95% in less than 10 minutes. Another advantage of the process of this invention resides in the fact that the co-precipitates contain a high content of active ingredient and from that, it may be possible to achieve pharmaceutical formulations which are less voluminous and more particularly, soft gelatin capsules of small size.

I-PROGESTERONE

1. Preparation of solid dispersions according to the invention

A-Preparation of physical mixtures

Physical mixtures containing 20, 30 or 50% w/w of progesterone in polyvinylpyrrolidone (Kollidon 30 BASF) were prepared by stirring for 10 minutes with a Mixer TURBULA. For each sample, the total amount per industrial batch was 5 g.

B-Preparation of co-precipitates of progesterone

The physical mixtures containing various proportions of progesterone were dissolved in a sufficient amount of absolute ethanol and the solid dispersions were obtained by evaporating off the solvent under the following conditions:

the speed of rotation of the flask was 100 Rd/min.

the temperature of the water bath was increased to 90° C.

the pressure in the inside of the flask was gradually increased to 200 millibars to prevent strong boiling of alcohol and then when the solution showed a viscous appearance, the pressure was again decreased to 50 millibars. The remaining alcohol was quickly removed and the co-precipitate which appeared in the form of a very stable white foam was easily recoverable by scratching the bottom of the flask with a spatula.

The thus-obtained samples were kept for 48 hours in an exsiccator before being ground and sieved to a grain size <100 pm.

C-Preparation of co-precipitates of progesterone-polyvinylpyrrolidone-polysorbate 80

The co-precipitates were prepared by the above process and then provided the most complete guaranties relating to stability. The following examples which relate to the more particular case of progesterone are only given as a way of illustration without limiting it in any manner.

TABLE 1 preparation of co-precipitates 20% w/w with polysorbate 80

| | Progesterone | Polyvinyl pyrrolidone | Solution of polysorbate 80 in ethanol (5 g/l) | Absolute ethanol |
|---|---|---|---|---|
| with 1% of polysorbate 80 | 1 g | 3.95 g | 10 ml | 80 ml |
| with 5% of polysorbate 80 | 1 g | 3.75 g | 50 ml | 40 ml |
| with 10% of polysorbate 80 | 1 g | 3.50 g | 100 ml | 0 |

TABLE 2 preparation of co-precipitates 30% w/w with polysorbate 80

| | Progesterone | Polyvinyl pyrrolidone | Solution of polysorbate 80 in ethanol (5 g/l) | Absolute ethanol |
|---|---|---|---|---|
| with 1% of polysorbate 80 | 1.5 g | 3.45 g | 10 ml | 100 ml |
| with 5% of polysorbate 80 | 1.5 g | 3.25 g | 50 ml | 60 ml |
| with 10% of polysorbate 80 | 1.5 g | 3.00 g | 100 ml | 10 ml |

TABLE 3 preparation of co-precipitates at 50% w/w with polysorbate 80

| | Progesterone | Polyvinyl pyrrolidone | Solution of polysorbate 80 in ethanol (5 g/l) | Absolute ethanol |
|---|---|---|---|---|
| with 1% of polysorbate 80 | 2.5 g | 2.45 g | 10 ml | 120 ml |
| with 5% of polysorbate 80 | 2.5 g | 2.25 g | 50 ml | 70 ml |
| with 10% of polysorbate 80 | 2.5 g | 2.00 g | 100 ml | 20 ml |

2-Study of the Kinetics of dissolution

A-Experimental method

The device for measuring utilized for the galenic control of the solid dispersions consisted of three members:-an apparatus for dissolution Dissolutest PT 6 from Erweka-a peristaltic pump 502 SR from Watson Marlow and-a spectrophotometer coupled with an automatic apparatus for dissolution, from SAFAS.

Each test of dissolution was carried out in one liter of degassed water at 37° C. and a pH close to neutral. A sample weighing about 5 mg of progesterone (i.e. 25 mg of co-melting or co-precipitate) was introduced into each of the six reactors at time TO with a speed of stirring of the paddles of 100 rpm. The dosing through UV absorption at 250 nm was performed continuously, and in closed circuit using a multi-channel peristaltic pump connecting the beakers of the Dissolutest apparatus, to the dishes of the spectrophotometer. The latter was linked to a recorder and to a printing machine to permit the measurement at constant intervals of every 3 minutes of the variations of the optical density, themselves being proportional to the variations of concentration of the active ingredient in the medium of dissolution.

B-Results

B.1-Kinetics of dissolution of the co-precipitate of Progesterone-PVP

The kinetics of dissolution of progesterone starting with the solid dispersions containing 20, 30 and 50% w/w of active ingredient are shown in Table 1. These results indicate that the rate of release of the hormone was dependent on the content of active ingredient in the co-precipitate. It was effectively noticed a rate of dissolution near 95% in 10 minutes for the co-precipitates at 20% w/w versus 55% and 18% for the co-precipitates at 30 and 50% w/w. This result showed that the best kinetics were obtained with the less concentrated solid dispersions, that is likely linked with a greater dispersion of the active ingredient within the co-precipitate when its content was low in the sample.

On the other side, it is interesting to point out that the kinetics of dissolution of the co-precipitates with 20% w/w were more rapid than those recorded at the time of the preliminary studies with samples of the same concentration. The result may be attributed to changes in the conditions of production. While decreasing the pressure and increasing the temperature of the water bath, the evaporation of the solvent was made easier and the crystallization of the active ingredient which remains incompletely crystallized or in a more or less amorphous state, was inhibited and then the active ingredient was more soluble.

B.2-Kinetics of dissolution of the co-precipitates of progesterone/PVP/Polysorbate 80

The kinetics of dissolution of progesterone starting from solid dispersions containing 20, 30 and 50% w/w of active ingredient with various proportions without or with 1, 5 or 10% w/w of polysorbate 80 are illustrated in the table IV, V, VI and VII.

TABLE IV

| Time | PROGESTERONE-PVP co-precipitates after manufacture | | |
|---|---|---|---|
| (minutes) | 20% | 30% | 50% |
| 0 | 0 | 0 | 0 |
| 3 | 77.32 | 33.49 | 5.55 |
| 6 | 88.65 | 45.79 | 9.76 |
| 9 | 92.93 | 53.38 | 17.06 |
| 12 | 95.31 | 57.61 | 18.73 |
| 15 | 96.74 | 62.85 | 22.30 |
| 18 | 97.77 | 65.71 | 23.73 |
| 21 | 98.38 | 68.01 | 27.38 |
| 24 | 99.03 | 71.11 | 30.39 |
| 27 | 99.82 | 74.68 | 33.01 |
| 30 | 99.90 | 77.79 | 35.07 |
| 33 | 99.90 | 80.39 | 37.46 |
| 36 | 99.90 | 83.17 | 39.12 |
| 39 | 99.90 | 85.26 | 41.34 |
| 42 | 99.90 | 87.46 | 43.14 |
| 45 | 99.90 | 88.01 | 44.82 |
| 48 | 99.90 | 89.28 | 46.58 |
| 51 | 99.90 | 91.26 | 48.80 |
| 54 | 99.90 | 92.46 | 50.55 |
| 57 | 99.90 | 94.20 | 51.11 |
| 60 | 99.90 | 94.92 | 52.06 |

TABLE V

| Time | PROGESTERONE-PVP 20% co-precipitates after manufacture with polysorbate 80 | | |
|---|---|---|---|
| (minutes) | 1% | 5% | 10% |
| 0 | 0 | 0 | 0 |
| 3 | 87.30 | 86.54 | 80.26 |
| 6 | 94.20 | 94.55 | 92.69 |

TABLE V-continued

| Time | PROGESTERONE-PVP 20% co-precipitates after manufacture with polysorbate 80 | | |
|---|---|---|---|
| (minutes) | 1% | 5% | 10% |
| 9 | 97.15 | 98.90 | 97.40 |
| 12 | 99.50 | 99.60 | 100 |
| 15 | 99.80 | 100 | 100 |
| 18 | 100 | 100 | 100 |
| 21 | 100 | 100 | 100 |
| 24 | 100 | 100 | 100 |
| 27 | 100 | 100 | 100 |
| 30 | 100 | 100 | 100 |

TABLE VI

| Time | PROGESTERONE-PVP 30% precipitates after manufacture with polysorbate 80 | | |
|---|---|---|---|
| (minutes) | 1% | 5% | 10% |
| 0 | 0 | 0 | 0 |
| 3 | 79.59 | 83.44 | 28.66 |
| 6 | 88.88 | 93.60 | 91.04 |
| 9 | 92.85 | 96.93 | 96.01 |
| 12 | 96.74 | 98.40 | 95 |
| 15 | 98.23 | 99.40 | 99.70 |
| 18 | 99.86 | 99.79 | 100 |
| 21 | 100 | 100 | 100 |
| 24 | 100 | 100 | 100 |
| 27 | 100 | 100 | 100 |
| 30 | 100 | 100 | 100 |

TABLE VII

| Time | PROGESTERONE-PVP co-precipitates after manufacture with polysorbate 80 | | |
|---|---|---|---|
| (minutes) | 20% | 30% | 50% |
| 0 | 0 | 0 | 0 |
| 3 | 22.38 | 36.82 | 44.91 |
| 6 | 37.93 | 51.90 | 60.10 |
| 9 | 46.42 | 61.50 | 69.70 |
| 12 | 54.12 | 67.22 | 74.40 |
| 15 | 58.65 | 71.98 | 78.90 |
| 18 | 62.38 | 76.36 | 83.50 |
| 21 | 65.15 | 80.47 | 89.84 |
| 24 | 68.49 | 81.66 | 93.96 |
| 27 | 70.63 | 83.04 | 95.55 |
| 30 | 72.38 | 84.52 | 96.79 |
| 33 | 74.28 | 86.31 | 98.25 |
| 36 | 75.39 | 87.49 | 98.49 |
| 39 | 77.14 | 88.49 | 100 |
| 42 | 78.65 | 89.12 | 100 |
| 45 | 80.23 | 90.71 | 100 |
| 48 | 81.57 | 91.76 | 100 |
| 51 | 82.38 | 92.58 | 100 |
| 54 | 82.93 | 92.93 | 100 |
| 57 | 83.88 | 93.17 | 100 |
| 60 | 85.15 | 93.92 | 100 |

TABLE VIII

| Time | PROGESTERONE-PVP co-precipitates after 6 months storage at 4° C. | | |
|---|---|---|---|
| (minutes) | 20% | 30% | 50% |
| 0 | 0 | 0 | 0 |
| 3 | 78.87 | 32.22 | 8.01 |
| 6 | 86.80 | 42.77 | 15 |

TABLE VIII-continued

| Time | PROGESTERONE-PVP co-precipitates after 6 months storage at 4° C. | | |
|---|---|---|---|
| (minutes) | 20% | 30% | 50% |
| 9 | 89.10 | 48.65 | 20.79 |
| 12 | 91 | 52.30 | 25.39 |
| 15 | 92.90 | 56.26 | 29.76 |
| 18 | 94.60 | 58.49 | 33.33 |
| 21 | 96 | 60.71 | 37.14 |
| 24 | 97.80 | 63.17 | 40.24 |
| 27 | 98.80 | 65.28 | 42.93 |
| 30 | 100 | 68.41 | 46.03 |
| 33 | 100 | 70.23 | 47.93 |
| 36 | 100 | 71.82 | 51.11 |
| 39 | 100 | 73.96 | 52.14 |
| 42 | 100 | 75.07 | 54.20 |
| 45 | 100 | 78.88 | 56.35 |
| 48 | 100 | 79.93 | 57.62 |
| 51 | 100 | 80.95 | 59.84 |
| 54 | 100 | 82.06 | 60.95 |
| 57 | 100 | 83.09 | 62.54 |
| 60 | 100 | 83.80 | 64.20 |

TABLE IX

| Time | PROGESTERONE-PVP co-precipitates after 6 months storage at room temperature | | |
|---|---|---|---|
| (minutes) | 20% | 30% | 50% |
| 0 | 0 | 0 | 0 |
| 3 | 83.33 | 30.87 | 12.40 |
| 6 | 90.79 | 42.14 | 22.69 |
| 9 | 93.25 | 47.62 | 30.47 |
| 12 | 95.30 | 53.57 | 37.77 |
| 15 | 96.90 | 55.95 | 42.85 |
| 18 | 97.90 | 60.79 | 47.69 |
| 21 | 98.80 | 62.30 | 52.22 |
| 24 | 99.80 | 64.20 | 55.70 |
| 27 | 100 | 67.90 | 58.48 |
| 30 | 100 | 70.48 | 61.98 |
| 33 | 100 | 71.98 | 64.68 |
| 36 | 100 | 75.16 | 66.81 |
| 39 | 100 | 76.90 | 69.67 |
| 42 | 100 | 78.57 | 71.58 |
| 45 | 100 | 80.32 | 72.93 |
| 48 | 100 | 81.83 | 75.63 |
| 51 | 100 | 82.78 | 77.23 |
| 54 | 100 | 83.01 | 78.48 |
| 57 | 100 | 83.65 | 79.99 |
| 60 | 100 | 85.32 | 81.35 |

TABLE X

| Time | PROGESTERONE-PVP co-precipitates after 6 months storage at 37° C. | | |
|---|---|---|---|
| (minutes) | 20% | 30% | 50% |
| 0 | 0 | 0 | 0 |
| 3 | 82.69 | 43.73 | 18.02 |
| 6 | 90.55 | 65.63 | 32.30 |
| 9 | 96.42 | 71.50 | 42.54 |
| 12 | 97.69 | 74.92 | 51.67 |
| 15 | 98.96 | 77.22 | 58.10 |
| 18 | 99.44 | 78.09 | 64.21 |
| 21 | 100 | 80.01 | 68.33 |
| 24 | 100 | 81.77 | 71.91 |
| 27 | 100 | 83.09 | 76.03 |
| 30 | 100 | 83.96 | 79.13 |
| 33 | 100 | 84.28 | 80.79 |
| 36 | 100 | 85.58 | 83.89 |
| 39 | 100 | 86.22 | 85.72 |

TABLE X-continued

| Time | PROGESTERONE-PVP co-precipitates after 6 months storage at 37° C. | | |
|---|---|---|---|
| (minutes) | 20% | 30% | 50% |
| 42 | 100 | 87.34 | 86.75 |
| 45 | 100 | 88.65 | 88.76 |
| 48 | 100 | 89.20 | 90.86 |
| 51 | 100 | 89.84 | 91.26 |
| 54 | 100 | 90.46 | 82.26 |
| 57 | 100 | 91.19 | 93.56 |
| 60 | 100 | 91.98 | 94.66 |

3-Study of the kinetics of dissolution after storage

A-Kinetics of dissolution of the co-precipitates of Progesterone-PVP

The kinetics of dissolution of progesterone starting from solid dispersions containing 20, 30 and 50% w/w of active ingredient after six months storage at 4° C., 20° C. and 37° C. are shown in tables VIII to X. As previously, it has been noticed that the rate of release of the hormone depends on its content in the co-precipitate. However, a comparison between the kinetics of dissolution after six months of storage, as compared to those measured with the same freshly-produced products, show that the increase in the temperature of storage seems to improve the rate of dissolution of progesterone in the most concentrated co-precipitates. The most significative result has been obtained with the co-precipitate with 50% w/w, stored at 37° C. for which a rate of dissolution of 95% after one hour was obtained as compared to 52% for the same product freshly produced.

B-Kinetics of dissolution of the co-precipitates of progesterone-PVP-polysorbate 80

The kinetics of dissolution of progesterone starting from a solid dispersion containing various proportions of polysorbate 80 and after storage for 6 months at 4° C., 20° C. and 37° C. are shown in the tables X, XI and XII. These results indicate that the kinetics of release of the hormone starting from co-precipitates stored for 6 months at 4°, 20° and 37° C. do not present any significant difference and are practically superposable to those recorded on freshly produced products. Temperature does not seem to play a determinant role in the conservation of the samples containing polysorbate 80 during the first 6 months of storage.

C-Comparative study of the phasma level of progesterone

RIA method after chromatography extraction of progesterone after oral administration to an empty stomach in 8 healthy menopausal female volunteers. (Cross-over study in hospitalized volunteers which had previously fasted the evening before, meal given after taking performed the fourth hour following the ingestion of the product).

TABLE XI

| Studied compound | Expression of the results | Cmax (ng/ml) | Tmax (h) | AUC (ng. ml[1].b) | Ratio of the geometric averages of the AUC vs. Utrogestan 200 mg |
|---|---|---|---|---|---|
| Co-precipitate of the invention 2 × 100 mg | Mean<br>SEM<br>min–max<br>CV | 115.46<br>26.73<br>7.80–231.58<br>0.68 | 0.69<br>0.09<br>0.50–1.00<br>0.38 | 144.71<br>34.28<br>18.62–335.98<br>0.69 | 5.66 |

TABLE XI-continued

| Studied compound | Expression of the results | Cmax (ng/ml) | Tmax (h) | AUC (ng. ml[1].b) | Ratio of the geometric averages of the AUC vs. Utrogestan 200 mg |
|---|---|---|---|---|---|
| Co-precipitate of the invention 2 × 70 mg | Mean | 67.25 | 0.75 | 73.99 | 3.90 |
| | SEM | 21.20 | 0.09 | 22.46 | |
| | min–max | 6.39–167.62 | 0.50–1.00 | 15.36–209.95 | |
| | CV | 0.91 | 0.36 | 0.90 | |
| Co-precipitate of the invention 2 × 35 mg | Mean | 10.82 | 0.69 | 13.39 | 0.56 |
| | SEM | 5.24 | 0.09 | 3.80 | |
| | min–max | 2.52–47.82 | 0.50–1.00 | 5.47–10.07 | |
| | CV | 1.40 | 0.38 | 0.84 | |
| Utrogestan ® 2 × 100 mg | Mean | 8.61 | 2.06 | 23.51 | |
| | SEM | 3.51 | 0.58 | 4.91 | |
| | min–max | 0.57–27.14 | 1–6 | 7.13–51.90 | |
| | CV | 1.19 | 0.80 | 0.65 | |

® Utrogestan is a brand name of a preparation based on micronized Progesterone

II-ESTRADIOL

1. Preparation of solid dispersions of the invention

A-Raw materials

The used raw materials were estradiol as the hemihydrate, art.680025 batch 24056446 from Schering AG (Berlin, Germany), polyvinylpyrrolidone (Kollidon 30 no. 56.0902 from BASF AG 67056 Ludwigshafen Germany). Tween 80 (polyoxyethylene sorbitan mono oleate AB 397). (ICI Chemicals, Niederlassung der deutsche ICI GMBH Goldschmidtstr. 100 D 4300 Essen 1) and Absolute ethanol (no. EEC 603.002.00.5) from Distillery Hauguel 76700 Gonfreville l'Orcher (F).

B-Apparatus

The apparatus to be used for the production of the solid dispersions were an electronic weighing machine A 120 Sartorius from OSI 141 rue de Javel 75015 Paris and a rotative evaporator RE Büchi, from Roucaire 20 avenue de l'Europe 78143 Velizy (F).

C-Preparation of the solid dispersions by dissolution-evaporation

The physical mixtures containing 10% estradiol w/w had the following composition: 0.5 g of estradiol, 4.25 g of PVP, 0.25 g of Tween 80 i.e. 50 ml of a 5 g/l solution in absolute ethanol and 20 ml of absolute ethanol enough for dissolving both estradiol and PVP. These mixtures were dissolved each in a sufficient amount of absolute ethanol. About 50 ml ethanol were needed for each gram of estradiol, 10 mol of ethanol per gram of PVP. The solid dispersions were obtained by evaporating the solvent under reduced pressure (p=200 millibars) for 15 minutes, and then the pressure was reduced to its minimum (about 40 millibars) for 15 minutes. The temperature of the water bath was 60° C. and the speed of rotation of the flask was 100 rounds/minute. The recovered samples were placed in an exsiccator for 47 hours and then were ground and screened. The galenical tests were performed on samples having granulometry lower than 100 micrometers.

2-Study of the kinetics of dissolution

A-Experimental method

The system of measurements used for the galenical control of the solid dispersions was made of two members: an apparatus of dissolution DISSOLUTEST DT 6 from ERWEKA |Euraf 55 rue Deschanel 92400 Courbevoie (France)| and a peristaltic pump 505 SR WATSON-MARLOW from Prolabo. Each test of dissolution was performed in one liter of degassed distilled water at 37° C. and at a pH near neutral. A sample of 4 mg of estradiol (i.e. 25 mg co-precipitate) was introduced in each of the six reactors at time t=0 and the speed of stirring of the paddles was 100 rounds/min. The dosages by UV (absorption at 278 nm), were performed continuously and in a closed circuit of a multi-channel peristaltic pump, connecting the beakers of the Dissolutest to the dishes of the spectrophometer. The latter was linked to a recorder and to a printing machine to permit the measurement at steady intervals of every 3 minutes of the variations of the optical density, themselves being proportional to the variations of the concentration of the active ingredient in the dissolution medium.

B-Results

The kinetics of dissolution of estradiol from the solid dispersions at 10% w/w are presented in FIG. 1. From this table, it may be seen that for the co-precipitates with 10% w/w of estradiol, an instantaneous dissolution which allows one to reach a percentage of dissolved compound of at least 65% in 3 minutes and at least 75% in 15 minutes.

TABLE XII

| Time | Estradiol 10%-PVP 75% Polysorbate 80 - 5% w/w co-precipitates | | | | | |
|---|---|---|---|---|---|---|
| (minutes) | Dish 1 | Dish 2 | Dish 3 | Dish 4 | Dish 5 | Dish 6 |
| 0 | 0 | 0 | 0 | 0 | 0 | 0 |
| 3 | 67.36 | 67.36 | 67.36 | 63.15 | 67.36 | 67.36 |
| 6 | 71.57 | 71.51 | 71.51 | 63.15 | 71.57 | 71.57 |
| 9 | 71.51 | 71.51 | 71.51 | 63.15 | 71.57 | 71.57 |
| 12 | 71.57 | 75.78 | 75.78 | 67.36 | 75.78 | 75.78 |
| 15 | 75.78 | 75.78 | 75.78 | 67.36 | 75.78 | 75.78 |
| 18 | 71.57 | 75.78 | 75.78 | 67.36 | 75.78 | 75.78 |
| 21 | 75.78 | 75.78 | 75.78 | 67.36 | 75.78 | 75.78 |
| 24 | 75.78 | 75.78 | 75.78 | 67.36 | 75.78 | 75.78 |
| 27 | 75.78 | 75.78 | 75.78 | 67.36 | 75.78 | 75.78 |
| 30 | 80 | 75.78 | 80 | 67.36 | 80 | 80 |
| 33 | 84.21 | 75.78 | 80 | 67.36 | 80 | 80 |
| 33 | 84.21 | 75.78 | 80 | 67.36 | 80 | 80 |

III-MIXTURES OF PROGESTERONE-ESTRADIOL

1-Production of solid dispersions of the invention

A-Raw materials

The used raw materials were the same as those used in the case of estradiol (chapter IV) to which progesterone was added (USP and EP batch 347 JA) from Upjohn Company Fine Chemical Division, Kalamazoo, Mich. 40991 (USA).

B-Apparatus

The apparatus was also the same than that used in the case of estradiol.

C-Production of solid dispersions by dissolution/evaporation

The performed co-precipitates had the following composition: 2.5 g of progesterone, 0.05 g of estradiol, 2.2 g of PVP and 0.25 g i.e. 50 ml of a solution at 5 g/l of Tween 80 in absolute ethanol. 103 ml of absolute ethanol were needed for the complete dissolution of the various components (50 ml absolute ethanol for 1 g of progesterone, 10 ml for 1 g of estradiol). The solid dispersions were obtained by evaporation of the solvent under vacuum (P=200 millibars) for 25 minutes, and then the pressure was decreased to its minimum (about 40 millibars) for 35 minutes. The temperature of the water bath was 60° C. and the speed of rotation of the flask was 100 rounds/minute. The thus-recovered samples were placed in an exsiccator for 48 hours and then were ground and sieved. The galenical tests were performed on samples having a granulometry lower than 100 micrometers. The co-precipitates obtained before staying in the exsiccator were in the form of a crystalline block, pale yellow or white, and small crystalline clusters were also recovered.

2-Study of the kinetics of dissolution

These tests of dissolution were performed in water and the used co-precipitates contained 50% progesterone and 1% estradiol. Two tests were performed: one with 200 mg of powder per liter of water and the other with 20 mg of powder per liter of water. The performance of these two tests may be explained by the fact that estradiol cannot be detected in a sample containing 20 mg of powder per liter of water and it had been necessary to use a sample of 200 mg of powder per liter of water to be able to detect estradiol.

Results: Test 1 (200 mg powder for 1 liter water)

TABLE XIII

| | Content in estradiol | | | Content in progesterone | | |
|---|---|---|---|---|---|---|
| Time (min.) | mg/l | Percentage in relation to theoretical content | Percentage in relation to the measured content | mg/l | Percentage in relation to the theoretical content | Percentage in relation to the measured content |
| 3 | <0.3 | <15 | <25 | 0.78 | 0.8 | 1.0 |
| 6 | <0.3 | <15 | <25 | 4.56 | 4.6 | 6.0 |
| 9 | 0.46 | 23 | 38.3 | 6.33 | 6.3 | 8.3 |
| 12 | 0.76 | 38 | 63.3 | 6.58 | 6.6 | 8.6 |
| 15 | 0.82 | 41 | 68.3 | 6.30 | 6.3 | 8.2 |
| 18 | 0.86 | 43 | 71.7 | 6.43 | 6.4 | 8.4 |

Test 2 (20 mg powder per liter of water)

TABLE XIV

| | Content in estradiol | | | Content in progesterone | | |
|---|---|---|---|---|---|---|
| Time (min.) | mg/l | Percentage in relation to theoretical value | Percentage in relation to the determined content | mg/l | Percentage in relation to the theoretical value | Percentage in relation to the determined content |
| 3 | ND | | | 0.27 | 2.7 | 3.5 |
| 6 | ND | | | 2.99 | 29.9 | 39.0 |
| 9 | ND | | | 3.87 | 38.7 | 50.5 |
| 12 | ND | | | 4.28 | 42.8 | 55.9 |
| 15 | ND | | | 4.49 | 44.9 | 58.6 |
| 18 | ND | | | 4.54 | 45.4 | 59.3 |

ND: Not detectable

3-Profiles of dissolution of the solid mixture progesterone-estradiol in water

Figure 2:
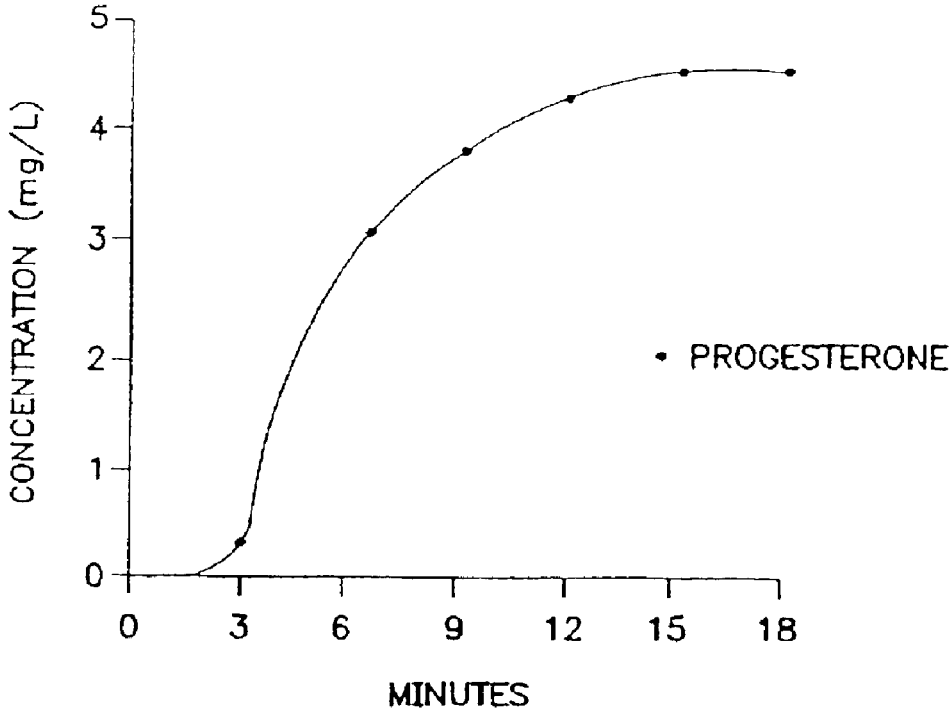
Figure 3:
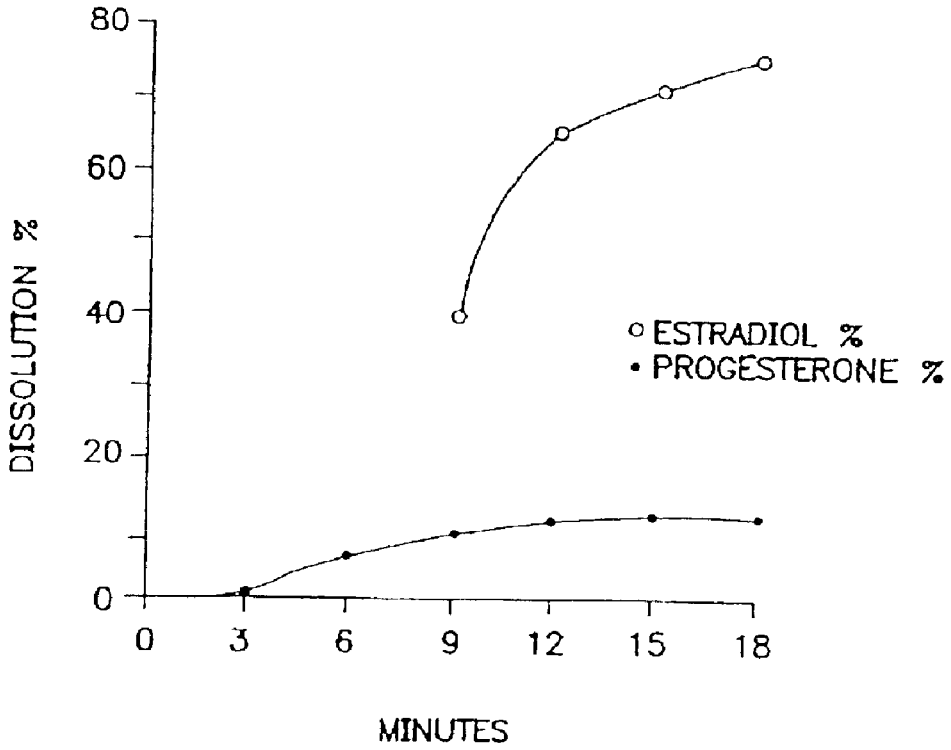
FIGS. 3 and 4 are the percentage of dissolution of the compositions in water.
Figure 4:
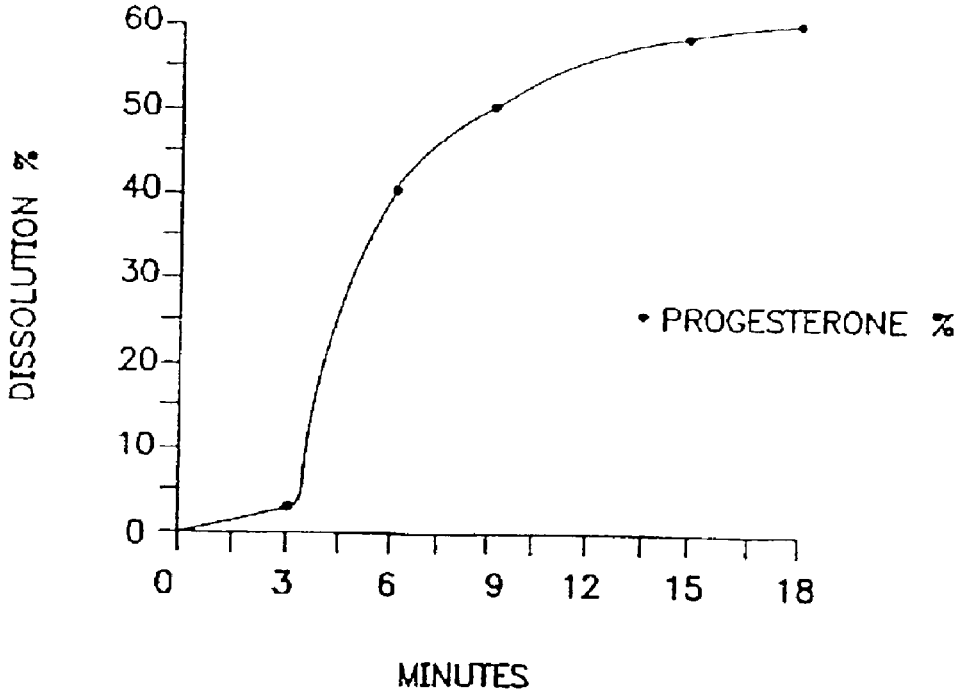

The curves of dissolution versus time are presented below: FIG. 1: (test of dissolution in water of 200 mg of powder per liter), FIG. 2: (test of dissolution in water of 20 mg of powder per liter), FIG. 3: (test of dissolution in water of 200 mg of powder per liter) and FIG. 4: determination of the percentage of progesterone dissolved in water starting of 20 mg of powder per liter of water.

IV-SOLID DISPERSIONS WITH FENOFIBRATE

1-Production of the solid dispersions of the invention

A-Raw materials

Fenofibrate (batch F 0092×100) from Schweizerhalt France-Deshors 17 Bd de Montmorency 75016 Paris, polyvinylpyrrolidone (Kollidon 30 - Nr 56 - 0902) from BASF AG 67056 Ludwigshafen Germany, Tween 80 (polyoxyethylene sorbitan monooleate) batch AB 397 (ICI Chemicals, Niederlassung der deutsche ICI GMBH, Goldschmidstr 100 D-4300 Essen 1) and absolute ethanol from Distillery Hauguel 76700 Gonfreville l'Orcher (F).

B-Apparatus

The needed material was exactly the same as that which had been used to produce the foregoing co-precipitates.

C-production of the solid dispersions by dissolution-evaporation

Five series of co-precipitates were achieved, each including 6 different samples.

TABLE XV

| | Series | | | | |
|---|---|---|---|---|---|
| | 1 | 2 | 3 | 4 | 5 |
| Fenofibrate | 2.5 gr | 2 gr | 1.5 gr | 1 gr | 0.5 gr |
| PVP K30 | 2.25 gr | 2.75 gr | 3.25 gr | 3.75 gr | 4.25 gr |
| Tween 80 | 0.25 gr | 0.25 gr | 0.25 gr | 0.25 gr | 0.25 gr |
| Absolute ethanol | 103 ml | 81 ml | 61 ml | 41 ml | 21 ml |

The solid dispersions were produced by evaporating under vacuum (P=205 millibars) for 25 minutes and then the pressure was decreased to its minimum (40 millibars) for 25 minutes. The temperature of the water bath was 60° C. and the speed of rotation of the flask was 100 rounds per minute. The duration of the evaporation was adapted, depending on the amount of absolute ethanol added for dissolving the products and then as a function of the series of the co-precipitates. The Samples with 2.5 g of fenofibrate had a yellowish appearance and formed a pellet more or less viscous, after one hour of evaporation at the minimal pressure.

The more the pressure was decreased (the amount of absolute ethanol added, decreasing from this fact), the more the recovered samples were clumsy, in the form of fine powder or granules. The color was white and bright and the co-precipitates appeared as being very dry. The thus-recovered samples were placed in an exsiccator for 48 hours and then were ground and sieved. The galenical tests were performed on samples of grain size lower than 100 micrometers.

2-Study of the kinetics of dissolution

A-Experimental method

This was identical to that used for the study of the kinetics of dissolution for the co-precipitates of estradiol.

B-Results

The maximal solubility of fenofibrate in water had been previously determined which was less than 3 mg/l. The co-precipitates produced above respectively contained 50%, 40%, 30%, 20% and 10% by weight of fenofibrate. When someone wanted to introduce in the reactors an amount of fenofibrate which allowed the total solubilization in 1 liter of water, he would need to weigh respectively 6 mg, 7.5 mg, 10 mg, 15 mg and 30 mg of co-precipitates. This accuracy in this measurement which was due to minute but unavoidable losses due to handling, cannot be achieved.

Therefore, it had been decided to prepare a calibrating range at 5 mg/l as for progesterone and to determine the kinetics of dissolution while introducing an equivalent amount of co-precipitate. This study permitted to quantify the amount of solubilized fenofibrate and in the course of this test, a recrystallization of fenofibrate had been observed. The results are shown in tables XVI and XVII respectively, the calibrating range and the kinetics of dissolution of fenofibrate in the co-precipitates at 10% w/w (randomly selected series which was representative of a phenomenon common to the other co-precipitates).

TABLE XVI

| Time | Calibrating range of Fenofibrate at 5 mg/l | | | | | |
|---|---|---|---|---|---|---|
| (minutes) | Dish 1 | Dish 2 | Dish 3 | Dish 4 | Dish 5 | Dish 6 |
| 0 | 0 | 0 | 0 | 0 | 0 | 0 |
| 3 | 95.26 | 95.26 | 98.94 | 93.68 | 94.21 | 93.15 |
| 6 | 92.1 | 92.1 | 95.78 | 91.05 | 92.1 | 90.52 |
| 9 | 87.89 | 87.89 | 91.05 | 86.31 | 87.89 | 85.78 |
| 12 | 83.68 | 83.68 | 86.31 | 82.1 | 83.15 | 80.52 |
| 15 | 80.52 | 80.52 | 83.15 | 78.42 | 80 | 76.84 |
| 18 | 77.89 | 77.36 | 80 | 75.26 | 77.36 | 74.21 |
| 21 | 74.73 | 74.73 | 76.84 | 71.57 | 73.68 | 71.05 |
| 24 | 72.1 | 72.1 | 73.68 | 68.94 | 71.05 | 68.42 |
| 27 | 70 | 70 | 71.57 | 66.84 | 68.94 | 66.31 |
| 30 | 68.42 | 67.89 | 69.47 | 64.73 | 67.36 | 64.73 |

The decrease of these kinetics of dissolution was exclusively due to the sensitivity of this formulation to the light and to the fact that the dosage was performed by UV Spectro-photometry at 278 nm, that resulted in a degradation of the formulation. This degradation was absolutely not due to the method of preparation of the co-precipitates but only to the technique of reading.

TABLE XVII

| Time | Co-precipitates fenotibeate 10% - PVP 25% Polysorbate 80 - 5% w/w | | | | | |
|---|---|---|---|---|---|---|
| (minutes) | Dish 1 | Dish 2 | Dish 3 | Dish 4 | Dish 5 | Dish 6 |
| 0 | 0 | 0 | 0 | 0 | 0 | 0 |
| 3 | 60.52 | 34.21 | 59.47 | 57.36 | 55.26 | 61.95 |
| 6 | 45.26 | 13.15 | 51.57 | 42.63 | 23.15 | 31.95 |
| 9 | 36.31 | 10.52 | 34.20 | 36.84 | 14.52 | 13.15 |
| 12 | 31.15 | 9.42 | 31.57 | 34.23 | 9.42 | 11.52 |
| 15 | 30 | 8.94 | 28.94 | 32.1 | 9.42 | 11.52 |
| 18 | 28.94 | 8.94 | 30.52 | 30.05 | 8.94 | 10 |
| 21 | 27.89 | 8.42 | 27.36 | 29.43 | 8.94 | 10 |
| 24 | 28.94 | 8.42 | 27.36 | 29.42 | 8.942 | 10 |
| 27 | 26.84 | 8.42 | 25.26 | 30.52 | 8.94 | 10 |
| 30 | 25.78 | 8.42 | 26.31 | 27.89 | 8.94 | 9.42 |
| 33 | 25.26 | 8.42 | 26.31 | 26.84 | 8.42 | 9.47 |
| 36 | 25.26 | 8.42 | 24.73 | 27.89 | 8.42 | 9.47 |
| 39 | 25.26 | 8.42 | 23.68 | 29.47 | 8.42 | 9.47 |
| 42 | 25.26 | 8.42 | 23.68 | 27.36 | 8.42 | 9.47 |
| 45 | 25.26 | 8.42 | 23.68 | 27.36 | 8.42 | 9.47 |
| 48 | 24.73 | 8.42 | 23.68 | 27.36 | 8.42 | 9.47 |
| 51 | 24.73 | 8.42 | 24.73 | 26.84 | 8.42 | 9.47 |
| 54 | 26.31 | 8.42 | 22.63 | 26.84 | 8.42 | 9.47 |
| 57 | 23.68 | 8.94 | 23.15 | 26.84 | 8.42 | 9.47 |
| 60 | 23.68 | 8.94 | 23.15 | 27.36 | 8.42 | 9.47 |

Herein also the UV Spectro-photometry was wholly responsible for the decrease of the kinetics of dissolution.

V-SOLID DISPERSIONS WITH MEDROXY PROGESTERONE ACETATE

1-Production of the solid dispersions of the invention

Five series of co-precipitates were realized each including six samples.

The amount of Medroxy progesterone acetate in each series was 0.5 g and that of polyvinylpyrrolidone ranged from 2 to 5 g. The solid dispersions were prepared according to the method described in example IV.

The solubility of Medroxy progesterone acetate in water is very low. The dosage of the amount of Medroxy progesterone acetate thus dissolved in water was determined by spectrophotometry at 241 nm.

The percentage of dissolved compound was about complete in 30 minutes at room temperature.

Various modification of the process and products of the invention may be made without departing from the spirit or scope thereof and it is to be understood that the invention is intended to be limited only as defined by the appended claims.

What we claim is:

1. A process for the production of a solid dispersion of 1 to 20% by weight of a surface active agent, 10 to 60% by weight of at least one therapeutic agent selected from the group consisting of progesterone and a mixture of progesterone and estradiol or an ester or ether thereof in a hydrophilic carrier having enhanced solubility in an aqueous media comprising dissolving the therapeutic agent in a volatile organic solvent containing a very hydrophilic polymer *and the surface active agent in the said percentage* and without strong heat or vacuum evaporating the solvent to dryness to form a co-precipitate of therapeutic agent [and], hydrophilic polymer *and surface active agent*.

2. The process of claim 1 wherein the co-precipitate is ground and screened to obtain a uniform powder.

3. The process of claim 1 wherein the evaporation to dryness of the organic solution is carried out in a fluidized bed of air.

4. The process of claim 1 wherein the volatile organic solvent is an oxygenated solvent or a chlorinated solvent.

5. The process of claim 1 wherein the volatile organic solvent is an alkanol.

6. The process of claim 1 wherein the volatile organic solvent is methylene chloride.

7. The process of claim 1 wherein the volatile organic solvent is selected from the group consisting of ethanol, isopropanol and terbutanol.

8. The process of claim 1 wherein the very hydrophilic polymer is selected from the group consisting of polyvinylpyrrolidones, N-methylpyrrolidones, N-methylcaprolactam and the N-methylpiperidin 2-ones.

9. The process of claim 1 wherein the polymer is polyvinyl pyrrolidones having a molecular weight ranging from [10.00] *10,000* to 50,000.

10. The process of claim 1 wherein the surface-active agent is a non-ionic surface-active agent.

11. The process of claim 1 wherein the non-ionic surface active agent is selected from the group consisting of polyoxyethylenic ester of sorbitan and saturated and unsaturated fatty acids having at least 8 carbon atoms, polyoxyethylenic ethers of fatty alcohols having at least 8 carbon atoms, polyoxyethylenic ethers of fatty alcohols having at least 8 carbon atoms and polyoxyethylenic esters of stearic acids.

12. The process of claim 1 wherein the surface-active agent is a polysorbate.

13. A solid dispersion with enhanced bioavailability of 1 to 20% by weight of a surface active agent, 10 to 60% by weight of at least one therapeutic agent selected from the group consisting of progesterone and an agent selected from the group consisting of progesterone and a mixture of progesterone and estradiol or an ester or ether thereof in a hydrophilic carrier having enhanced solubility in an aqueous media comprising dissolving the therapeutic agent in a volatile organic solvent containing a very hydrophilic polymer *and the surface active agent in the said percentage* and without strong heat or vacuum evaporating the solvent to dryness to form a co-precipitate of therapeutic agent [and], hydrophilic polymer *and surface active agent*.

14. A solid dispersion with enhanced bioavilability of claim 13 wherein the therapeutic agent is a mixture of estradiol or one of its ester or ethers, and progesterone.

15. A pharmaceutical composition containing the solid dispersions obtained by claim 2 wherein the solid dispersion of therapeutic agents are admixed with an inert non-toxic pharmaceutically-acceptable carrier.

16. A pharmaceutical composition of claim 15 wherein the inert carrier is constituted by neutral pellets of starch.

17. A pharmaceutical composition of claim 15 wherein the inert carrier is an aqueous sterile medium.

18. A method for treating disorders connected with a hormonal insufficiency comprising administering to a female patient in need of such a therapy, a safe but effective amount of a therapeutic agent consisting of progesterone or progesterone and estradiol or an ether or ester thereof in the form of a solid dispersion obtained by the process of claim 1.

19. The method of claim 18 wherein the hormonal insufficiency is [a luteal] *an estro-progestative* insufficiency and the therapeutic agent is *a mixture of estradiol and* progesterone.

20. The method of claim 18 wherein the hormonal insufficiency is an estro-progestative insufficiency and the therapeutic agent is a mixture of estradiol and progesterone.

* * * * *